US009885725B2

(12) United States Patent
Fukuyama et al.

(10) Patent No.: US 9,885,725 B2
(45) Date of Patent: Feb. 6, 2018

(54) MALDI ANALYSIS OF HYDROPHOBIC COMPOUNDS USING 2(3),5-DIHYDOXYBENZOATE WITH A LONG ALKYL CHAIN AS AN ADDITIVE TO MALDI MATRIX

(71) Applicants: SHIMADZU CORPORATION, Kyoto-shi, Kyoto (JP); HIROSHIMA UNIVERSITY, Hiroshima (JP)

(72) Inventors: Yuko Fukuyama, Kyoto (JP); Shunsuke Izumi, Hiroshima (JP)

(73) Assignees: SHIMADZU CORPORATION, Kyoto (JP); HIROSHIMA UNIVERSITY, Hiroshima (JP)

( * ) Notice: Subject to any disclaimer, the term of this patent is extended or adjusted under 35 U.S.C. 154(b) by 11 days.

(21) Appl. No.: 14/495,814

(22) Filed: Sep. 24, 2014

(65) Prior Publication Data
US 2015/0276756 A1  Oct. 1, 2015

(30) Foreign Application Priority Data

Mar. 27, 2014 (JP) .................................. 2014-065904

(51) Int. Cl.
*G01N 33/68* (2006.01)
(52) U.S. Cl.
CPC ................................ *G01N 33/6851* (2013.01)
(58) Field of Classification Search
CPC ........... G01N 33/6851; G01N 33/6848; G01N 33/6845; B01D 15/327; Y10T 436/24;
(Continued)

(56) References Cited

U.S. PATENT DOCUMENTS 5,506,348 A    4/1996 Pieles
7,354,996 B2*  4/2008 Matsuo .............. G01N 33/6842
                                          250/282
(Continued)

FOREIGN PATENT DOCUMENTS

JP          6-322274 A    11/1994
JP       2005-328391      11/2005
(Continued)

OTHER PUBLICATIONS

Weidner et al. "MALDI-TOF imaging mass spectrometry of artifacts in "dried droplet" polymer samples", Anal. Bional. Chem., 2011. v. 401, pp. 127-134.*
(Continued)

*Primary Examiner* — Yelena G Gakh
(74) *Attorney, Agent, or Firm* — Cheng Law Group, PLLC

(57) ABSTRACT

The present invention provides a mass spectrometry method that can achieve analysis with high sensitivity using a matrix additive capable of improving ionization efficiency in mass spectrometry. A mass spectrometry method comprising the steps of: forming a mixed crystal for mass spectrometry on a target plate for mass spectrometry, the mixed crystal comprising a sample to be analyzed, a matrix, and a matrix additive selected from the group consisting of a 2,5-dihydroxybenzoate and a 3,5-dihydroxybenzoate that are represented by the following formula (I):

(Continued)

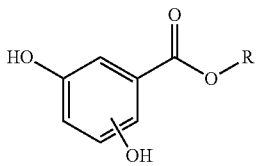

(I)

where R represents an alkyl group having 4 to 14 carbon atoms; and irradiating the mixed crystal with laser to detect the sample to be analyzed.

4 Claims, 5 Drawing Sheets

(58) Field of Classification Search
CPC ........... Y10T 436/25; B01J 2219/00725; B01J 2219/00702; B01J 2219/0063; G06F 19/28; G06F 19/18; G06F 19/24; G06F 19/22; G06F 19/03
See application file for complete search history.

(56) References Cited

U.S. PATENT DOCUMENTS

| | | |
|---|---|---|
| 7,550,301 B2 | 6/2009 | Wang et al. |
| 8,119,416 B2 | 2/2012 | Wang et al. |
| 2004/0142487 A1 | 7/2004 | Wang et al. |
| 2004/0152913 A1* | 8/2004 | Caprioli ............... C07F 9/10 560/55 |
| 2005/0224710 A1 | 10/2005 | Matsuo et al. |
| 2006/0240562 A1 | 10/2006 | Caprioli et al. |
| 2012/0208295 A1 | 8/2012 | Wang et al. |
| 2013/0062570 A1 | 3/2013 | Fukuyama et al. |
| 2014/0084152 A1 | 3/2014 | Fukuyama et al. |

FOREIGN PATENT DOCUMENTS

| | | |
|---|---|---|
| JP | 2013-68598 A | 4/2013 |
| JP | 2013-190250 A | 9/2013 |

OTHER PUBLICATIONS

Bashir, Sajid et al., "Matrix-assisted laser desorption/ionization mass spectrometry with re-engineered 2.5-dihydroxybenzoic acid derivative", Analyst, The Royal Society of Chemistry, 2003, vol. 128, No, 12, pp. 1452-1457.
Nihel, Ken-ichi et al., "Molecular Design of Multifunctional Food Additives: Antioxidative Antifungal Agents". Journal of Agricultural and Food Chemistry, 2004, vol. 52, No. 16, pp. 5011-5020.
Krokhin, Oleg V., "Sequence-Specific Retention Calculator. Algorithm for Peptide Retention Prediction in Ion-Pair RP-HPLC: Application to 300- and100-A Pore Size C18 Sorbents", Analytical Chemistry, 2006, vol. 78, No. 22, pp. 7785-7795.
Fukuyama, Yuko et al., "Alkylated Dihydroxybenzoic Acid as a MALDI Matrix Additive for Hydrophobic Peptide Analysis", Analytical Chemistry, 2012, vol. 84, pp. 4237-4243, and Correction: 2014: vol. 86, p. 5187.
Browne, C. A. et al., "The Isolation of Peptides by High-Performance Liquid Chromatography Using Predicted Elution Positions", 1982, Analytical Biochemistry, vol. 124, pp. 201-208.
Guyot, B. et al., "Esterification of Phenolic Acids from Green Coffee with an Immobilized Lipase from Candida Antarctica in Solvent-Free Medium", Biotechnology Letters, 1997, vol. 19, No. 6, pp. 529-532.
Nihei, Ken-ichi et al., "Molecular Design of Multifunctional Food Additives. Antioxidative Antifungal Agents", Journal of Agricultural and Food Chemistry, 2004, vol. 52, No. 16, pp. 5011-5020.

* cited by examiner

(a) CHCA+ADHB-ES

(b) CHCA

Fig.2

|  | CHCA+ADHB-ES | CHCA |
|---|---|---|
|  | 1 mm | 1 mm |
| humanin (m/z 2688.2) | (a) | (e) |
| β-amyloid 1-11 (m/z 1326.3) | (b) | (f) |
| CHCA (m/z 189.9) | (c) | (g) |
| ADHB-ES (m/z 266.0) | (d) | |

Fig.3

| no. | SSRCalc Hydrophobicity | sensitivity improvement rate (fold) | CHCA+ADH8-ES | CHCA |
|---|---|---|---|---|
| 1 | 54.8 | 100 | | |
| 2 | 53.8 | 10 | | |
| 3 | 51.1 | 100 | | |
| 4 | 50.2 | 100 | | |
| 5 | 50.0 | 100 | | |
| 6 | 49.5 | 10 | | |
| 7 | 45.8 | 10 | | |
| 8 | 45.2 | 10 | | |
| 9 | 13.5 | 1 | | |
| 10 | 10.8 | 1 | | |
| 11 | 5.2 | 1 | | |

# MALDI ANALYSIS OF HYDROPHOBIC COMPOUNDS USING 2(3),5-DIHYDROXYBENZOATE WITH A LONG ALKYL CHAIN AS AN ADDITIVE TO MALDI MATRIX

BACKGROUND OF THE INVENTION

Field of the Invention

The present invention relates to a mass spectrometry method applicable to medical field and drug discovery field, and especially relates to MALDI-MS (Matrix-Assisted Laser Desorption/Ionization Mass Spectrometry) application. More precisely, the present invention relates to a mass spectrometry method using a specific compound as a matrix additive, and a matrix additive for mass spectrometry.

Disclosure of the Related Art

Conditions for achieving efficient ionization of a molecule to be analyzed in MALDI (Matrix-Assisted Laser Desorption/Ionization) mass spectrometry have been researched.

For example, JP-A-2005-326391 (Patent Document 1) discloses a method in which a hydrophobic peptide, especially an NBS-modified peptide obtained by previously modifying a peptide with 2-nitrobenzenesulfenyl (NBS) group, is subjected to mass spectrometry using, as a matrix, α-cyano-3-hydroxycinnamic acid (3-CHCA), 3-hydroxy-4-nitrobenzoic acid (3H4NBA), or a mixture of them so that the hydrophobic peptide is more efficiently ionized as compared to when a general matrix such as α-cyano-4-hydroxycinnamic acid (4-CHCA) or 2,5-dihydrobenzoic acid (DHB) is used.

J. Agric. Food Chem., 2004, 52(16), pp. 5011-5020 (Non-Patent Document 1) discloses alkyl esters of 3,4-dihydroxybenzic acid as food additives.

Biotechnology Letters, Vol. 19, No. 6, June 1997, pp. 529-532 (Non-Patent Document 2) discloses the yield of esterification between 2,5-dihydroxybenzoic acid and octanol.

Patent Document 1: JP-A-2005-326391
Non-Patent Document 1: Journal of Agricultural and Food Chemistry, 2004, Vol. 52, No. 16, pp. 5011-5020
Non-Patent Document 2: Biotechnology Letters, June 1997, Vol. 19, No. 6, pp. 529-532

SUMMARY OF THE INVENTION

According to the MALDI mass spectrometry method disclosed in Patent Document 1, a certain level of ionization enhancement effect is obtained when modification of a molecule to be analyzed is performed, but sufficient ionization efficiency is not achieved when such modification is not performed. Particularly, the MALDI mass spectrometry method has a problem that the ionization efficiency of a molecular species difficult to ionize by MALDI, such as a hydrophobic peptide, is low.

An object of the present invention is to provide a substance that is capable of easily and efficiently improving ionization efficiency in mass spectrometry without performing modification of a molecule to be analyzed.

The present inventors have intensively studied, and as a result, have found that 2,5-dihydroxybenzoate having an alkyl group with a certain number of carbon atoms does not function as a matrix, but the object of the present invention can be achieved by using such a compound as a matrix additive. This finding has led to the completion of the present invention.

Specifically, the present inventors have found that the ionization efficiency of a hydrophobic peptide in MALDI mass spectrometry is improved by using, as a matrix additive, an alkyl 2,5- or 3,5-dihydroxybenzoate compound. Particularly, Example 2 that will be described later revealed that when a hydrophobic peptide humanin was analyzed using a mixed solution of octyl 2,5-dihydroxybenzoate (C8-ADHB-ES) and a general matrix α-cyano-4-hydroxycinnamic acid (4-CHCA) [a solution obtained by mixing CHCA: 10 mg/mL (50% ACN/0.05% TFA aqueous solution) and C8-ADHB-ES: 5 mg/mL (50% ACN/0.05% TFA aqueous solution) in a ratio of 10:1 (v/v)], the limit of detection became two orders of magnitude lower, that is, sensitivity was improved 100-fold as compared to when 4-CHCA was used alone.

Such a matrix additive was found to have the effect of improving the sensitivity of a hydrophobic peptide humanin in MALDI mass spectrometry. However, the sensitivity of a hydrophobic peptide difficult to ionize in MALDI mass spectrometry is also expected to be further improved.

Another object of the present invention is to provide a mass spectrometry method that can achieve analysis with high sensitivity using a matrix additive capable of improving ionization efficiency in mass spectrometry without performing modification (specifically, labeling or the like) of a molecule to be analyzed. Particularly, an object of the present invention is to provide a mass spectrometry method that can achieve analysis with high sensitivity using a matrix additive capable of improving ionization efficiency in MALDI mass spectrometry without performing modification (specifically, labeling or the like) of a molecule to be analyzed.

The present inventors have intensively studied, and as a result, have found that 2,5-dihydroxybenzoate having an alkyl group with a certain number of carbon atoms is ineffective as a matrix, but the object of the present invention can be achieved by using such a compound as a matrix additive. This finding has led to the completion of the present invention.

The present inventors have further intensively studied, and as a result, have found that a molecular species difficult to ionize, such as a hydrophobic compound, can also be efficiently ionized and analyzed with high sensitivity by laser irradiation of the outer peripheral region of a crystal for mass spectrometry formed on a target plate for mass spectrometry using, as a matrix additive, an alkyl 2,5- or 3,5-dihydroxybenzoate compound. This finding has led to the completion of the present invention.

The present invention includes the following.

(1) A mass spectrometry method comprising the steps of:
forming a mixed crystal for mass spectrometry on a target plate for mass spectrometry, the mixed crystal comprising a sample to be analyzed, a matrix, and a matrix additive selected from the group consisting of a 2,5-dihydroxybenzoate and a 3,5-dihydroxybenzoate that are represented by the following formula (I):

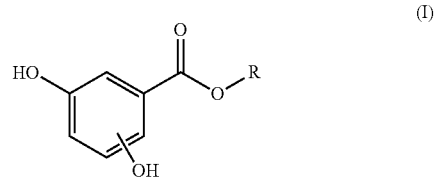

where R represents an alkyl group having 4 to 14 carbon atoms; and irradiating the mixed crystal with laser to detect the sample to be analyzed.

(2) The mass spectrometry method according to the above (1), wherein in the step of detecting the sample to be analyzed, an outer peripheral region of the mixed crystal for mass spectrometry is irradiated with laser.

(3) The mass spectrometry method according to the above (1) or (2), wherein the mixed crystal for mass spectrometry has a substantially circular shape on a surface in contact with the target plate for mass spectrometry, an average outer diameter of the outer peripheral region is an average diameter of the substantially circular shape, and an average inner diameter of the outer peripheral region is 80% or more of the average outer diameter.

(4) The mass spectrometry method according to any one of the above (1) to (3), wherein the sample to be analyzed is a hydrophobic compound.

(5) The mass spectrometry method according to any one of the above (1) to (4), wherein the sample to be analyzed is a hydrophobic peptide. It is to be noted that in the present invention, the term "peptide" includes proteins.

(6) The mass spectrometry method according to any one of the above (1) to (5), wherein as the matrix, a compound is used which is selected from the group consisting of α-cyano-3-hydroxycinnamic acid (3-CHCA), α-cyano-4-hydroxycinnamic acid (4-CHCA), 3-hydroxy-4-nitrobenzoic acid (3H4NBA), 2,5-dihydroxybenzoic acid, sinapic acid, and 1,5-diaminonaphthalene.

(7) A matrix additive for mass spectrometry, which is selected from the group consisting of a 2,5-dihydroxybenzoate and a 3,5-dihydroxybenzoate that are represented by the following formula (I):

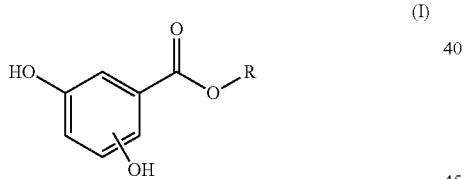

(I)

where R represents an alkyl group having 4 to 14 carbon atoms.

According to the present invention, it is possible to provide a matrix additive capable of improving ionization efficiency of a molecule (especially, a hydrophobic peptide) to be analyzed by mass spectrometry.

The present invention makes it possible to achieve improvement in sensitivity for detection of a molecule (especially, a hydrophobic peptide) to be analyzed by mass spectrometry in mass spectrometric analysis.

In the present invention, when the outer peripheral region of a mixed crystal for mass spectrometry formed using a matrix additive selected from a 2,5-dihydroxybenzoate and a 3,5-dihydroxybenzoate that are represented by the above general formula (I) is irradiated with laser, a hydrophobic compound is more enriched in the outer peripheral region of the mixed crystal for mass spectrometry, which makes it possible to improve ionization efficiency of a molecule to be analyzed that is difficult to ionize, such as a hydrophobic compound, especially a hydrophobic peptide, in mass spectrometry and to achieve analysis with high sensitivity.

The method according to the present invention is particularly directed to a MALDI mass spectrometry method, and is suitable when an object to be analyzed is a hydrophobic compound and particularly suitable when an object to be analyzed is a hydrophobic peptide.

BRIEF DESCRIPTION OF THE DRAWINGS

FIG. 2 shows the results of MS imaging analysis in Example 1, including photographs of crystals formed in wells on a MALDI plate, and MS images of a hydrophobic peptide humanin, a hydrophilic peptide β-amyloid 1-11, 4-CHCA, and 4-CHCA+C8-ADHB-ES.

FIG. 3 shows the results of MS imaging analysis in Example 2, including photographs of crystals formed in wells on a MALDI plate, and MS images of respective peptides obtained using 4-CHCA+C8-ADHB-ES or 4-CHCA.

DETAILED DESCRIPTION OF THE INVENTION

[Matrix Additive]

Figure 1:
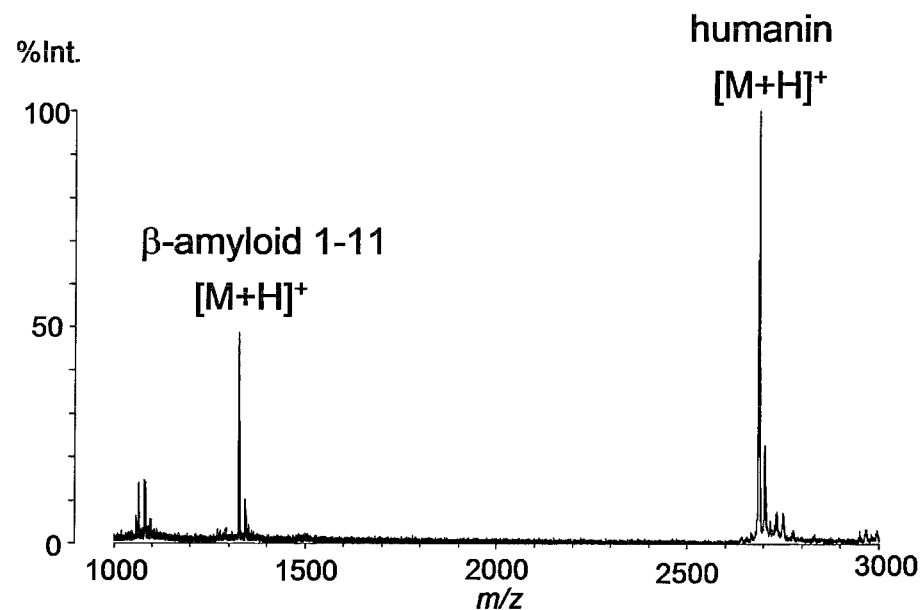
FIG. 1(a) shows the result of mass spectrometry using 4-CHCA+C8-ADHB-ES in Example 1, wherein the horizontal axis represents mass/charge (m/z) and the vertical axis represents ion relative intensity (% Int.)
FIG. 1(b) shows the result of mass spectrometry using 4-CHCA alone in Example 1, wherein the horizontal axis represents mass/charge (m/z) and the vertical axis represents ion relative intensity (% Int.).
Figure 1:
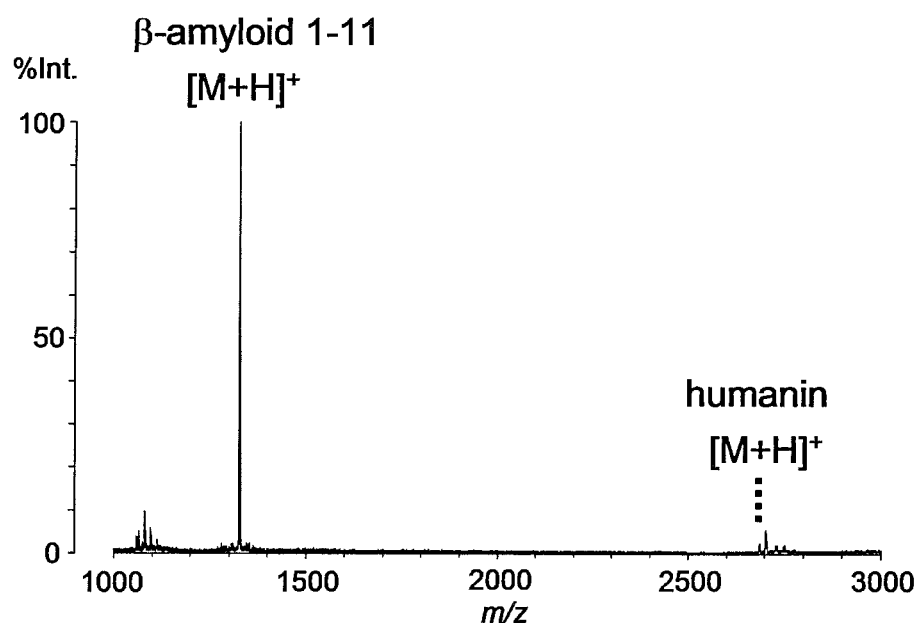

In the present invention, a 2,5- or 3,5-dihydroxybenzoate represented by the following formula (I) is used as a matrix additive for mass spectrometry:

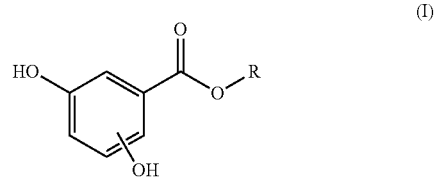

(I)

where R represents an alkyl group having 4 or more carbon atoms, specifically 4 to 14 carbon atoms, preferably 8 to 14 carbon atoms, more preferably 8 to 10 carbon atoms. The alkyl group may be linear or branched.

The compound represented by the above formula (I) is appropriately synthesized by those skilled in the art by an esterification reaction using 2,5- or 3,5-dihydroxybanzoic acid or a derivative thereof. For example, the compound represented by the above formula (I) can be synthesized by esterifying 2,5- or 3,5-dihydroxybenzoic acid using an electrophile represented by R—X (where R represents an alkyl group having 4 to 14 carbon atoms, preferably 8 to 14 carbon atoms, more preferably 8 to 10 carbon atoms, and X represents a halogen (F, Cl, Br or I) or another leaving group). In this case, the electrophile can be used in an amount of 1.0 to 2.0 equivalents per equivalent of the dihydroxybenzoic acid. As a solvent, acetone, tetrahydrofuran, dimethylformamide, or the like can be used. The reaction may be performed by heating under reflux for 2 hours or more.

The above compound does not have the ability to ionize an object to be analyzed alone and therefore does not function as a matrix. However, the use of the above compound in combination with a matrix makes it possible to enhance the ability of the matrix to ionize an object to be analyzed, thereby improving the limit of detection.

[Matrix]

A matrix to be used in combination with the additive according to the present invention is not particularly limited. The matrix may be appropriately selected from common matrixes by those skilled in the art. For example, the matrix to be used may be a compound selected from α-cyano-3-hydroxycinnamic acid (3-CHCA), α-cyano-4-hydroxycinnamic acid (4-CHCA), 3-hydroxy-4-nitrobenzoic acid (3H4NBA), 2,5-dihydroxybenzoic acid, sinapic acid, and 1,5-diaminonaphthalene. Among them, α-cyano-4-hydroxycinnamic acid (4-CHCA) can be preferably used.

[Object to be Analyzed by Mass Spectrometry]

An object to be analyzed by mass spectrometry using the method of the present invention is not particularly limited, and may be, for example, a molecule having a molecular weight of 500 to 30,000, preferably 1,000 to 10,000. The object to be analyzed by mass spectrometry is preferably a hydrophobic substance.

The degree of hydrophobicity of the hydrophobic substance is not particularly limited as long as it is at a level that can be regarded as hydrophobic based on any known hydrophobicity index or hydrophobicity calculation method. For example, the degree of hydrophobicity of the hydrophobic substance may be at a level that can be regarded as hydrophobic by those skilled in the art based on the BB Index (Bull and Breese Index). More specifically, the BB Index of the hydrophobic substance may be, for example, 1,000 or less, preferably −1,000 or less.

Alternatively, the degree of hydrophobicity of the hydrophobic substance may be at a level that can be regarded as hydrophobic by those skilled in the art based on the HPLC Index. The HPLC Index is a hydrophobicity index reported by C. A. Browne, H. P. J. Bennett, and S. Solomon in Analytical Biochemistry, 124, 201-208, 1982, and is also referred to as "HPLC/HFBA retention" because it is based on retention time in reversed-phase HPLC using, as an eluent, an aqueous acetonitrile solution containing 0.13% heptafluoro-n-butyric acid (HFBA). More specifically, the HPLC Index of the hydrophobic substance may be, for example, 40 or more, for example, 40 to 10,000, preferably 100 to 1,000.

Further, in the present invention, the degree of hydrophobicity of the hydrophobic substance may be at a level that can be regarded as hydrophobic by those skilled in the art based on SSRCalc Hydrophobicity. SSRCalc Hydrophobicity has been reported by Oleg V. Krokhin in Analytical Chemistry, 78, 7785-7795, 2006. SSRCalc Hydrophobicity is a hydrophobic index based on a peptide sequence-specific algorithm for prediction of retention times of peptides in RP-HPLC (Reversed-Phase High-Performance Liquid Chromatography), sequence-specific retention calculator (SSRCalc). The HPLC index or BB index predicts a retention time based on only information about amino acid composition, whereas SSRCalc Hydrophobicity predicts a retention time based on also primary and secondary peptide structures. In the present invention, when the object to be analyzed is a hydrophobic peptide, SSRCalc Hydrophobicity is suitable as an index of the degree of hydrophobicity. More specifically, SSRCalc Hydrophobicity may be, for example, 30 or more, preferably 40 to 90, more preferably 40 to 70.

Particularly, the matrix additive used in the present invention is highly effective in enhancing the ability of a matrix to ionize a hydrophobic peptide (in the present invention, the term "peptide" includes proteins).

The determination as to whether a peptide to be analyzed is hydrophobic or not may be made based on the BB Index, the HPLC Index, or SSRCalc Hydrophobicity, and preferably, SSRCalc Hydrophobicity. More specifically, the hydrophobic peptide may be a peptide containing, as constituent amino acids, more amino acids having a higher degree of hydrophobicity. Examples of such hydrophobic amino acids include isoleucine, leucine, valine, alanine, phenylalanine, proline, methionine, tryptophan, and glycine. Further, cysteine, tyrosine, and the like may also be included.

The hydrophobic peptide may be a peptide having not only such a primary structure but also a higher-order structure with a higher degree of hydrophobicity. Examples of such a hydrophobic peptide include peptides having a structure likely to interact with the surface of a hydrophobic stationary phase in a reversed-phase HPLC column.

[Formation of Crystal for Mass Spectrometry]

In the present invention, a mixed crystal for mass spectrometry is formed on a target plate for mass spectrometry, which comprises a sample to be analyzed, a matrix, and a matrix additive selected from a 2,5-dihydroxybenzoate and a 3,5-dihydroxybenzoate that are represented by the above formula (I).

In the present invention, the combination ratio of the matrix additive and the matrix is not particularly limited. For example, the matrix additive and the matrix for mass spectrometry may be combined to satisfy a quantitative relation such that the ratio of the matrix additive is 0.01 to 50 moles, preferably 0.01 to 1 mole per mole of the matrix.

In the present invention, the matrix additive is usually prepared as a mixed solution with the matrix. The mixed solution of the matrix and the additive can be usually prepared by preparing a matrix solution and an additive solution, respectively, and mixing the two solutions. As a solvent, for example, an aqueous acetonitrile (ACN)-trifluoroacetic acid (TFA) solution, an aqueous acetonitrile solution, an aqueous trifluoroacetic acid solution or the like can be used. The concentration of acetonitrile in the aqueous acetonitrile-trifluoroacetic acid solution may be, for example, 10 to 90 vol %, and the concentration of trifluoroacetic acid in the aqueous acetonitrile-trifluoroacetic acid solution may be, for example, 0.05 to 1 vol %.

The matrix additive may be prepared as, for example, a solution of 0.5 to 50 mg/mL, preferably 5 to 10 mg/mL, for example, 5 mg/mL. The matrix may be prepared as, for example, a solution of 1 mg/mL to a saturated concentration, preferably 1 to 10 mg/mL, for example, 10 mg/mL. For example, these additive solution and matrix solution may be mixed in a volume ratio of 10:1 to 1:10, for example 1:1.

A mixed crystal for mass spectrometry can be obtained through the step of forming, on a target plate for mass spectrometry, a liquid droplet of a mixture liquid containing, in a solvent, at least an analyte, a matrix, and the matrix additive, and the step of removing the solvent from the formed liquid droplet of the mixture liquid to obtain nonvolatile matter contained in the mixture liquid (i.e., at least the analyte, the matrix, and the matrix additive) as a residue. The thus obtained residue is a crystal for mass spectrometry. In this specification, the term "crystal for mass spectrometry" is synonymous with the term "residue".

As the target for mass spectrometry, a conductive metal plate usually used in MALDI mass spectrometry may be used. More specifically, a plate made of stainless steel or gold may be used.

A specific method for preparing a liquid droplet of the mixture liquid on a target plate is not particularly limited. For example, first, a sample solution containing an analyte, a matrix solution, and an additive solution are prepared separately from one another; or a sample solution containing an analyte and a mixture solution containing a matrix and an additive are prepared separately from each other. Then, these solutions are mixed to obtain a mixture liquid, and the obtained mixture liquid is dropped onto a target plate. Alternatively, these solutions may be mixed on a target plate by dropping these solutions onto the same position on the target plate (on-target mix). In the case of on-target mix, the order of dropping the solutions is not particularly limited.

The solvent of the mixture liquid may be selected from the group consisting of acetonitrile (ACN), trifluoroacetic acid (TFA), methanol (MeOH), ethanol (EtOH), tetrahydrofuran (THF), dimethylsulfoxide (DMSO), and water. Specific examples of the solvent of the mixture include an aqueous ACN-TFA solution, an aqueous ACN solution, an aqueous MeOH-TFA solution, an aqueous MeOH solution, an aqueous EtOH-TFA solution, an aqueous EtOH solution, an aqueous THF-TFA solution, an aqueous THF solution, an aqueous DMSO-TFA solution, and an aqueous DMSO solution. Among them, an aqueous ACN-TFA solution or an aqueous ACN solution may be preferably used. The concentration of ACN in the aqueous ACN-TFA solution may be, for example, 10 to 90 vol %, preferably 25 to 75 vol %, and the concentration of TFA in the aqueous ACN-TFA solution may be, for example, 0.05 to 1 vol %, preferably 0.05 to 0.1 vol %.

The volume of the liquid droplet of the mixture liquid is not particularly limited, and may be appropriately determined by those skilled in the art. When a well is provided on the target plate, the liquid droplet of the mixture liquid may be formed in the well. In this case, the liquid droplet is formed so as to have a volume that can be held in the well. More specifically, the liquid droplet may be formed so as to have a volume of about 0.1 µL to 2 µL, for example, about 0.5 µL.

Next, the solvent is removed from the liquid droplet of the mixture liquid on the target plate. The removal of the solvent includes natural evaporation of the solvent. The amount of the matrix contained per one residue (that is, per one crystal for mass spectrometry) generated by evaporation may be, for example, 1 to 1,000 nmol, preferably 10 to 100 nmol. As described above, the amount of the additive may be 0.01 to 50 times, preferably 0.05 to 0.5 times the amount of the matrix. The amount of the analyte may be in the range of 50 amol to 100 pmol or in the range of 100 amol to 50 pmol with respect to 25 nmol of the matrix.

The residue has a substantially circular shape on a surface in contact with the target plate. That is, the outer edge of the residue is substantially circular. The average diameter of the substantially circular shape may vary depending on the amount of the sample, the volume of the liquid droplet, the amount of the matrix, the composition of the solvent etc., but is for example 1 to 3 mm, preferably 1 to 2 mm. It is to be noted that the average diameter is the average of the lengths of line segments cut from lines passing through the center of gravity of the substantially circular shape by the outer edge of the residue.

In the present invention, the above specific matrix additive is used. Thereby, in the liquid droplet of the mixture liquid prepared on the target plate, a hydrophobic substance is uniformly present before the solvent is removed. However, the hydrophobic substance is not uniformly present in the residue obtained by removing the solvent but is localized in the outer peripheral region of the residue. More specifically, the hydrophobic substance is enriched in the outer peripheral region of the residue, and is therefore less likely to be present in a region inside the outer peripheral region of the residue. More specifically, 50 mol % or more, preferably 70 mol % or more of the entire hydrophobic substance present in the residue may be localized in the outer peripheral region of the residue.

The outer peripheral region of the residue where the hydrophobic substance is localized has a substantially annular (ring) shape. The average diameter of the outer edge of the outer peripheral region, that is, the average outer diameter of the outer peripheral region is the average of the lengths of line segments cut from lines passing through the center of gravity by the outer edge of the outer peripheral region, which is in agreement with the average diameter of the residue that has already been described. On the other hand, the average diameter of the inner edge of the outer peripheral region, that is, the average inner diameter of the outer peripheral region is the average of the lengths of line segments cut from lines passing through the center of gravity by the inner edge of the outer peripheral region, which is, for example, 80% or more, preferably 90% or more of the average outer diameter. The upper limit of the above range is not particularly limited, but is, for example, 99%.

When a substance (e.g., a hydrophilic substance) other than the hydrophobic substance is contained in the sample, as described above, the hydrophobic substance is locally present in the residue, whereas the substance other than the hydrophobic substance is uniformly present in the entire region of the residue including the central part of the residue in which the hydrophobic substance is less likely to be present. In such a case, the substance other than the hydrophobic substance is relatively more hydrophilic than the hydrophobic substance. More specifically, the substance other than the hydrophobic substance may be a substance whose BB Index is larger than −1,000, preferably larger than 1,000 or whose HPLC Index is smaller than 100, preferably smaller than 60.

Such localization of the hydrophobic substance is advantageous in that the hydrophobic substance as the analyte can be localized in a very small region. The localization of the analyte in a very small region makes it possible for the analyte to be densely present at a point irradiated with laser, thereby achieving analysis in high sensitivity.

Therefore, mass spectrometry in high sensitivity can be achieved not by irradiating the entire region of the residue (i.e., both the outer peripheral region and the region inside the outer peripheral region) with laser in a conventional manner but by irradiating only the ring-shaped outer peripheral region of the residue where the hydrophobic substance is localized with laser. However, in the present invention, the operation of irradiating the entire region of the mixed crystal for mass spectrometry with laser may be performed.

[Mass Spectrometer]

A mass spectrometer used in the present invention is not particularly limited as long as it is used in combination with a MALDI (Matrix-Assisted Laser Desorption/Ionization)

ion source. Examples of such a mass spectrometer include MALDI-TOF (Matrix-Assisted Laser Desorption/Ionization-Time-of-Flight) mass spectrometers, MALDI-IT (Matrix-Assisted Laser Desorption/Ionization-Ion Trap) mass spectrometers, MALDI-IT-TOF (Matrix-Assisted Laser Desorption/Ionization-Ion Trap-Time-of-Flight) mass spectrometers, and MALDI-FTICR (Matrix-Assisted Laser Desorption/Ionization-Fourier Transform Ion Cyclotron Resonance) mass spectrometers.

EXAMPLES

Hereinbelow, the present invention will be described more specifically with reference to examples, but is not limited to the following examples.
[Synthesis of Additive, Octyl 2,5-Dihydroxybenzoate]

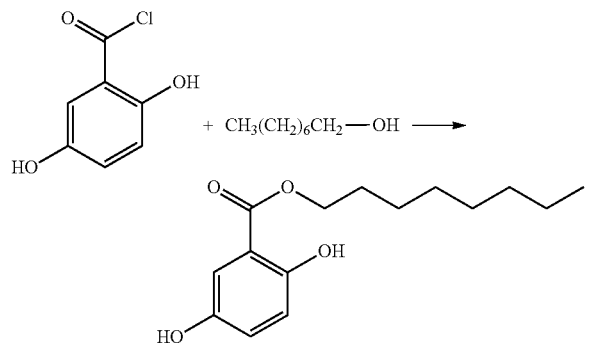

In anhydrous pyridine (10 mL), 1-octanol (10 mmol) was dissolved to obtain a solution. Then, an anhydrous ether solution of 2,5-hydroxybenzoic acid chloride (10 mmol) was dropped into the solution and stirred at room temperature for 8 hours. After cooled, the mixture was washed with a 1 M HCl aqueous solution and then water, and subjected to extraction with ether (100 mL) twice. The thus obtained ether layers were mixed, dried with anhydrous sodium sulfate, and subjected to solvent removal and then purification by silica gel column chromatography (developing solvent:hexane:ethyl acetate=8:2 (v/v)) to obtain a yellowish-white crystal in an amount of 0.80 g ($3.0 \times 10^{-3}$ mol) with a 30% yield.

Example 1

In this example, α-cyano-4-hydroxycinnamic acid (4-CHCA, Laser Bio) was used as a matrix, and octyl 2,5-dihydroxybenzoate (referred to as C8-ADHB-ES) was used as an additive.

(1) A 10 mg/mL 4-CHCA solution (in 50% ACN/0.05% TFA water (% is by volume; the same shall apply hereinafter)) and a 5 mg/mL C8-ADHB-ES solution (in 50% ACN/0.05% TFA water) were mixed in a ratio of 10/1 (v/v) to prepare a 4-CHCA+8-ADHB-ES solution.

(2) A 400 fmol/μL solution (in 50% ACN/0.05% TFA water) of a hydrophobic peptide humanin and a 400 fmol/μL solution (in 50% ACN/0.05% TFA water) of a hydrophilic peptide β-amyloid 1-11 were prepared and mixed in a ratio of 1:1 (v/v) to prepare a mixed solution of the hydrophobic peptide and the hydrophilic peptide (200 fmol/μL).

(3) The sample solution (0.5 μL) prepared in (2) and the 4-CHCA+C8-ADHB-ES solution (0.5 μL) prepared in (1) were dropped onto a MALDI plate and mixed (on-target mix).

(4) MS imaging analysis was performed using AXIMA Performance (Shimadzu Corporation) by linear TOF in positive mode.
(Conditions of MS Imaging Analysis)

Data was acquired by raster scanning an area of 4,000 μm×4,000 μm on the surface of a crystal in a well of a sample plate at 50 μm irradiation intervals so that each of a total of 6,561 points (81 points×81 points) was irradiated with two shots of laser. An MS image (distribution map obtained by MS imaging) shows a peak intensity distribution created based on mV of the m/z peak of [M+1-1]+ of a sample obtained at each of the points in the data. As a result, the distribution of a target sample on the crystal is shown.

A mass spectrum in this case is shown in FIG. 1(a) and the results of MS imaging analysis are shown in FIG. 2.

Comparative Example (1) A 10 mg/mL 4-CHCA solution (in 50% ACN/0.05% TFA water) was prepared.

(2) A 400 fmol/μL solution (in 50% ACN/0.05% TFA water) of a hydrophobic peptide humanin and a 400 fmol/μL solution (in 50% ACN/0.05% TFA water) of a hydrophilic peptide β-amyloid 1-11 were prepared and mixed in a ratio of 1:1 (v/v) to prepare a mixed solution of the hydrophobic peptide and the hydrophilic peptide (200 fmol/μL).

(3) The sample solution (0.5 μL) prepared in (2) and the matrix solution (0.5 μL) prepared in (1) were dropped onto a MALDI plate and mixed (on-target mix).

(4) MS imaging analysis was performed using AXIMA Performance (Shimadzu Corporation) by linear TOF in positive mode.

A mass spectrum in this case is shown in FIG. 1(b) and the results of MS imaging analysis are shown in FIG. 2.
(Results)

As shown in FIG. 1(b), when 4-CHCA was used alone, the hydrophilic peptide β-amyloid 1-11 was preferentially detected and the hydrophobic peptide humanin was hardly detected. In contrast, as shown in FIG. 1(a), when 4-CHCA+C8-ADHB-ES was used, the hydrophobic peptide humanin was more preferentially detected than the hydrophilic peptide β-amyloid 1-11.

FIG. 2 shows photographs of crystals formed in wells on the MALDI plate and MS images of the hydrophobic peptide humanin, the hydrophilic peptide β-amyloid 1-11, 4-CHCA, and 4-CHCA+C8-ADHB-ES.

As can be seen from the results of MS imaging (FIG. 2), when 4-CHCA+C8-ADHB-ES was used, humanin was detected mainly in the outer peripheral region of the matrix/sample mixed crystal, and β-amyloid 1-11 was detected mainly in the entire inner region of the crystal. At this time, the matrix 4-CHCA was detected mainly in the entire region of the crystal and ADHB-ES was detected mainly in the outer peripheral region of the crystal. On the other hand, when 4-CHCA was used, humanin was detected also in the inner region of the matrix/sample mixed crystal. At this time, β-amyloid 1-11 and 4-CHCA were detected in the entire inner region of the matrix/sample mixed crystal as in the case of using 4-CHCA+C8-ADHB-ES. Therefore, it was revealed that the use of 4-CHCA+ADHB-ES allows humanin to be enriched together with C8-ADHB-ES in the outer peripheral region so that the hydrophobic peptide is preferentially detected with high sensitivity.

Example 2: Irradiation of Outer Peripheral Region of Mixed Crystal with Laser

In this example, 11 kinds of peptides different in HPLC index (HPLC index: −60.2 to 200.0) were prepared as analytes and analyzed using α-cyano-4-hydroxycinnamic acid (4-CHCA, Laser Bio) as a matrix and octyl 2,5-dihydroxybenzoate (referred to as C8-ADHB-ES) as an additive to determine how many times detection sensitivity would be improved (sensitivity improvement rate) as compared to when a conventional matrix α-cyano-4-hydroxycinnamic acid (4-CHCA) was used alone.

(1) A 10 mg/mL 4-CHCA solution (in 50% ACN/0.05% TFA water) and a 5 mg/mL C8-ADHB-ES solution (in 50% ACN/0.05% TFA water) were mixed in a ratio of 10/1 (v/v) to prepare a 4-CHCA+C8-ADHB-ES solution.

(2) As a sample solution for detection limit evaluation, a 200 fmol/µL solution (in 50% ACN/0.05% TFA water) of each of the peptides, NF-kB inhibitor, melittin honey bee, β-amyloid 1-42, OVA-BIP hybrid peptide, humanin, [Gly14]-humanin, temporin A amide, MPG Δ NLS, β-amyloid 1-11, GPHRSTPESRAAV (SEQ ID No. 1), and β-conglycinin 165-178 was prepared. Further, as a sample for MS imaging evaluation, a mixed solution of these peptides (concentration of each peptide: 200 fmol/µL) was prepared.

(3) The sample solution or mixed sample solution (0.5 µL) prepared in (2) and the additive-containing matrix solution (0.5 µL) prepared in (1) were dropped onto a MALDI plate and mixed (on-target mix).

(4) Analysis was performed using AXIMA Performance (Shimadzu Corporation) by linear TOF in positive mode by manually irradiating the outer peripheral region of a mixed crystal formed using the sample solution in (3) with laser to evaluate the limit of detection. Further, a mixed crystal formed using the mixed sample solution in (3) was analyzed by MS imaging by performing raster scanning in the same manner as in Example 1.

Comparative Example (1) A 10 mg/mL 4-CHCA solution (in 50% ACN/0.05% TFA water) was prepared.

(2) As a sample solution for detection limit evaluation, a 200 fmol/µL solution (in 50% ACN/0.05% TFA water) of each of the peptides, NF-kB inhibitor, melittin honey bee, β-amyloid 1-42, OVA-BIP hybrid peptide, humanin, [Gly14]-humanin, temporin A amide, MPG Δ NLS, β-amyloid 1-11, GPHRSTPESRAAV (SEQ ID No. 1), and β-conglycinin 165-178 was prepared. Further, as a sample for MS imaging evaluation, a mixed solution of these peptides (concentration of each peptide: 200 fmol/µL) was prepared.

(3) The sample solution or mixed sample solution (0.5 µL) prepared in (2) and the matrix solution (0.5 µL) prepared in (1) were dropped onto a MALDI plate and mixed (on-target mix).

(4) Analysis was performed using AXIMA Performance (Shimadzu Corporation) by linear TOF in positive mode by manually irradiating the outer peripheral region of a mixed crystal formed using the sample solution in (3) with laser to evaluate the limit of detection. Further, a mixed crystal formed using the mixed sample solution in (3) was analyzed by MS imaging by performing raster scanning in the same manner as in Example 1.

(Results)

The SSRCalc Hydrophobicity and HPLC index of each of the peptides (analytes), and a sensitivity improvement rate (fold) determined for each of the peptides by dividing the detection limit of the peptide obtained using 4-CHCA used alone by the detection limit of the peptide obtained using 4-CHCA+C8-ADHB-ES are collectively listed in Table 1.

Sensitivity improvement rate=[Detection limit obtained using 4-CHCA alone]/[Detection limit obtained using 4-CHCA+C8-ADHB-ES]

TABLE 1

| analytes | | SSRCalc Hydrophobicity | HPLC Index | m/z (Av.) | sensitivity improvement rate (fold) |
|---|---|---|---|---|---|
| no. | name | | | | |
| 1 | NF-kB inhibitor | 54.8 | 200.0 | 2782.5 | 100 |
| 2 | melittin, honey bee | 53.8 | 117.8 | 2847.5 | 10 |
| 3 | β-amyloid 1-42 | 51.1 | 110.4 | 4515.1 | 100 |
| 4 | OVA-BIP hybrid peptide | 50.2 | 100.8 | 2291.5 | 100 |
| 5 | humanin | 50.0 | 117.4 | 2688.2 | 100 |
| 6 | [Gly14]-humanin | 49.5 | 120.3 | 2658.2 | 10 |
| 7 | temporin A, amide | 45.6 | 110.9 | 1397.8 | 10 |
| 8 | MPGΔNLS | 45.2 | 125.6 | 2767.2 | 10 |
| 9 | β-amyloid 1-11 | 13.5 | 1.4 | 1326.3 | 1 |
| 10 | GPHRSTPESRAAV | 10.6 | 3.3 | 1365.5 | 1 |
| 11 | β-conglycinin 165-178 | 5.2 | −60.2 | 1848.8 | 1 |

As shown in Table 1, the peptides having an SSRCalc Hydrophobicity of 45.2 or more were detected with 10- to 100-fold higher sensitivity when 4-CHCA+C8-ADHB-ES was used as compared to when 4-CHCA was used. Particularly, when 4-CHCA+C8-ADHB-ES was used, the peptides having an SSRCalc Hydrophobicity of 45.2 or more were detected in the outer peripheral region of the matrix/sample mixed crystal.

FIG. 3 shows photographs of crystals formed in wells on the MALDI plate and the results of MS imaging analysis of each of the peptides obtained using 4-CHCA+C8-ADHB-ES or 4-CHCA. As can be seen from FIG. 3, the peptides having an SSRCalc Hydrophobicity of 45.2 or more and found to be improved in sensitivity by using 4-CHCA+C8-ADHB-ES were detected mainly in the outer peripheral region of the matrix/sample mixed crystal. On the other hand, when 4-CHCA was used to analyze the hydrophilic peptides having an SSRCalc Hydrophobicity of 13.5 or less, and when 4-CHCA+C8-ADHB-ES was used to analyze the hydrophilic peptides having an SSRCalc Hydrophobicity of 13.5 or less, the hydrophilic peptides were detected mainly in the entire inner region of the sample/matrix mixed crystal.

These results revealed that when analyzed using a mixture of a common matrix and C8-ADHB-ES as an additive, the hydrophobic peptides are particularly enriched in the outer peripheral region of the matrix/sample mixed crystal and therefore can be analyzed with high sensitivity by irradiating the outer peripheral region with laser.

Example 3

In this example, a hydrophobic peptide (humanin; BB index: −5,800, HPLC index: 117.4, SSRCalc Hydrophobicity: 50.0) was analyzed using octyl 2,5-dihydroxybenzoate (referred to as C8-ADHB-ES) as an additive added to a matrix α-cyano-4-hydroxycinnamic acid (4-CHCA). For the purpose of comparison, the hydrophobic peptide was analyzed using α-cyano-4-hydroxycinnamic acid (CHCA) alone as a matrix.

(1) A 10 mg/mL 4-CHCA solution (in an aqueous 50% ACN/0.05% TFA solution (% is by volume; the same shall apply hereinafter)) and a 5 mg/mL C8-ADHB-ES solution (in an aqueous 50% ACN/0.05% TFA solution) were mixed in ratios of 1:1, 10:1, and 100:1 (v/v). The thus obtained matrix solutions were referred to as 4-CHCA+C8-ADHB-ES (1/1), 4-CHCA+C8-ADHB-ES (10/1), and 4-CHCA+C8-ADHB-ES (100/1), respectively.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and each of the matrix solutions (0.5 µL) prepared in (1) were dropped onto a MALDI plate and mixed (on-target mix).

(4) Analysis was performed using AXIMA Performance (Shimadzu Corporation) by linear TOF in positive and negative modes.

Comparative Example (1) A 10 mg/mL CHCA (Laser Bio) solution (in an aqueous 50% ACN/0.05% TFA solution) was prepared.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and the solution (0.5 µL) prepared in (1) were dropped onto a MALDI plate and mixed (on-target mix).

(4) Analysis was performed using AXIMA Performance (Shimadzu Corporation) by linear TOF in positive and negative modes.

When the additive-containing matrix 4-CHCA+C8-ADHB-ES (10/1) was used, the limit of detection was lowest in both positive (pos) and negative (neg) modes, and sensitivity was improved as compared to when 4-CHCH was used alone.

Example 4

In this example, a hydrophobic peptide (humanin) was analyzed using C8-ADHB-ES as an additive added to each of matrixes 2,5-dihydroxybenzoic acid (DHB), sinapic acid (SA), and 1,5-diaminonaphthalene (DAN) as in the case of Example 1 where 4-CHCA was used as a matrix. For the purpose of comparison, the hydrophobic peptide was analyzed using each of 2,5-dihydroxybenzoic acid (DHB), sinapic acid (SA), and 1,5-daminonaphthalene (DAN) alone as a matrix.

(1) Each of 10 mg/mL matrix solutions (4-CHCA, DHB, SA, and DAN) (in an aqueous 50% ACN/0.05% TFA solution) and a 5 mg/mL C8-ADHB-ES solution (in an aqueous 50% ACN/0.05% TFA solution) were mixed in a ratio of 10:1 (v/v) to prepare a matrix solution. The thus obtained matrix solutions were referred to as 4-CHCA+C8-ADHB-ES, DHB+C8-ADHB-ES, SA+C8-ADHB-ES, and DAN+C8-ADHB-ES, respectively.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and each of the matrix solutions (0.5 µL) prepared in (1) were dropped onto a MALDI plate and mixed (on-target mix).

(4) Analysis was performed using AXIMA Performance (Shimadzu Corporation) by linear TOF in positive and negative modes.

Comparative Example (1) Each of 10 mg/mL matrix solutions (4-CHCA, DHB, SA, and DAN) (in an aqueous 50% ACN/0.05% TFA solution) was prepared.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and each of the matrix solutions (0.5 µL) prepared in (1) were dropped onto a MALDI plate and mixed (on-target mix).

(4) Analysis was performed using AXIMA Performance (Shimadzu Corporation) by linear TOF in positive and negative modes.

TABLE 2

| | humanin (fmol/well) | |
|---|---|---|
| | positive mode | negative mode |
| 4-CHCA + C8-ADHB-ES | 0.1 | 1 |
| 4-CHCA | 10 | 100 |
| DHB + C8-ADHB-ES | 1 | 10 |
| DHB | 1 | 10 |
| SA + C8-ADHB-ES | 10 | 10 |
| SA | 10 | 100 |
| 1,5-DAN + C8-ADHB-ES | 10 | 100 |
| 1,5-DAN | 100 | 100 |

As can be seen from Table 2, in all the cases where the additive-containing matrix was used, sensitivity was the same or improved in both positive and negative modes as compared to when the matrix was used alone. More specifically, sensitivity was improved 100-fold in positive and negative modes when 4-CHCA+C8-ADHB-ES (10/1) was used, sensitivity was the same when DHB+C8-ADHB-ES (10/1) was used, sensitivity was improved 10-fold in negative mode when SA+C8-ADHB-ES (10/1) was used, and sensitivity was improved 10-fold in positive mode when DAN+C8-ADHB-ES (10/1) was used.

The results of Example 4 revealed that when the matrix was used in combination with the additive C8-ADHB-ES according to the present invention, sensitivity was improved in the order of 4-CHCA>SA>DAN.

Example 5

In this example, 4-CHCA was used as a matrix and alkyl 2,5-dihydroxybenzoates (ADHB-ES) different in the length of their alkyl chain were used as additives. More specifically, C1-ADHB-ES (methyl ester), C4-ADHB-ES (butyl ester), C6-ADHB-ES (hexyl ester), C8-ADHB-ES (octyl ester), C10-ADHB-ES (decyl ester), and C16-ADHB-ES (hexadecyl ester) were used.

(1) A 10 mg/mL solution (in an aqueous 50% ACN/0.05% TFA solution) of a matrix 4-CHCA and a 5 mg/mL solution (in an aqueous 50% ACN/0.05% TFA solution) of each of C1-ADHB-ES, C4-ADHB-ES, C6-ADHB-ES, C8-ADHB-ES, C10-ADHB-ES, and C16-ADHB-ES were mixed in a ratio of 10:1 (v/v) to prepare a matrix solution. The thus obtained matrix solutions were referred to as 4-CHCA+C1-ADHB-ES, 4-CHCA+C4-ADHB-ES, 4-CHCA+C6-ADHB-ES, 4-CHCA+C8-ADHB-ES, 4-CHCA+C10-ADHB-ES, and 4-CHCA+C16-ADHB-ES, respectively.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and each of the matrix solutions (0.5 µL) prepared in (1) were dropped onto a MALDI plate and mixed (on-target mix).

(4) Analysis was performed using AXIMA Performance (Shimadzu Corporation) by linear TOF in positive and negative modes.

Comparative Example (1) A 10 mg/mL 4-CHCA solution (in an aqueous 50% ACN/0.05% TFA solution) was prepared.

(2) Two amol/µL to 2 pmol/µL solutions (in an aqueous 50% ACN/0.05% TFA solution) of a hydrophobic peptide humanin were prepared.

(3) Each of the sample solutions (0.5 µL) prepared in (2) and the matrix solution (0.5 µL) prepared in (1) were dropped onto a MALDI plate and mixed (on-target mix).

(4) Analysis was performed using AXIMA Performance (Shimadzu Corporation) by linear TOF in positive and negative modes.

TABLE 3

|  | humanin (fmol/well) | |
| --- | --- | --- |
|  | positive mode | negative mode |
| 4-CHCA + C16-ADHB-ES | 1 | 10 |
| 4-CHCA + C10-ADHB-ES | 1 | 10 |
| 4-CHCA + C8-ADHB-ES | 0.1 | 1 |
| 4-CHCA + C6-ADHB-ES | 1 | 10 |
| 4-CHCA + C4-ADHB-ES | 10 | 100 |
| 4-CHCA + C1-ADHB-ES | 10 | 100 |
| 4-CHCA | 10 | 100 |

As can be seen from Table 3, sensitivity was improved in both positive and negative modes when each of 4-CHCA+C4-ADHB-ES, 4-CHCA+C6-ADHB-ES, 4-CHCA+C8-ADHB-ES, 4-CHCA+C10-ADHB-ES, and 4-CHCA+C16-ADHB-ES was used as compared to when the matrix was used alone. Particularly, sensitivity was most improved when 4-CHCA+C8-ADHB-ES was used. More specifically, when each of 4-CHCA+C6-ADHB-ES, 4-CHCA+C10-ADHB-ES, and 4-CHCA+C16-ADHB-ES was used, sensitivity was improved 10-fold in positive and negative modes, and when 4-CHCA+C8-ADHB-ES was used, sensitivity was improved 100-fold in positive and negative modes.

Example 6

In this example, 4-CHCA was used as a matrix and C8-ADHB-ES was used as an additive. For the purpose of comparison, analysis was performed using each of 4-CHCA and C8-ADHB-ES alone as a matrix.

(1) A 10 mg/mL solution (in an aqueous 50% ACN/0.05% TFA solution) of a matrix 4-CHCA and a 5 mg/mL C8-ADHB-ES solution (in an aqueous 50% ACN/0.05% TFA solution) were mixed in a ratio of 10:1 (v/v) to prepare a matrix solution (4-CHCA+C8-ADHB-ES).

(2) A 40 fmol/μL solution (in an aqueous 50% ACN/0.05% TFA solution) of a hydrophobic peptide humanin and a 40 fmol/μL solution (in an aqueous 50% ACN/0.05% TFA solution) of a hydrophilic peptide β-amyloid 1-11 were prepared and mixed in a ratio of 1:1 (v/v) to prepare a mixed solution.

(3) The sample solution (0.5 μL) prepared in (2) and the matrix solution (0.5 μL) prepared in (1) were dropped onto a MALDI plate and mixed (on-target mix).

(4) Analysis was performed using AXIMA Performance (Shimadzu Corporation) by linear TOF in positive mode.

Figure 4:
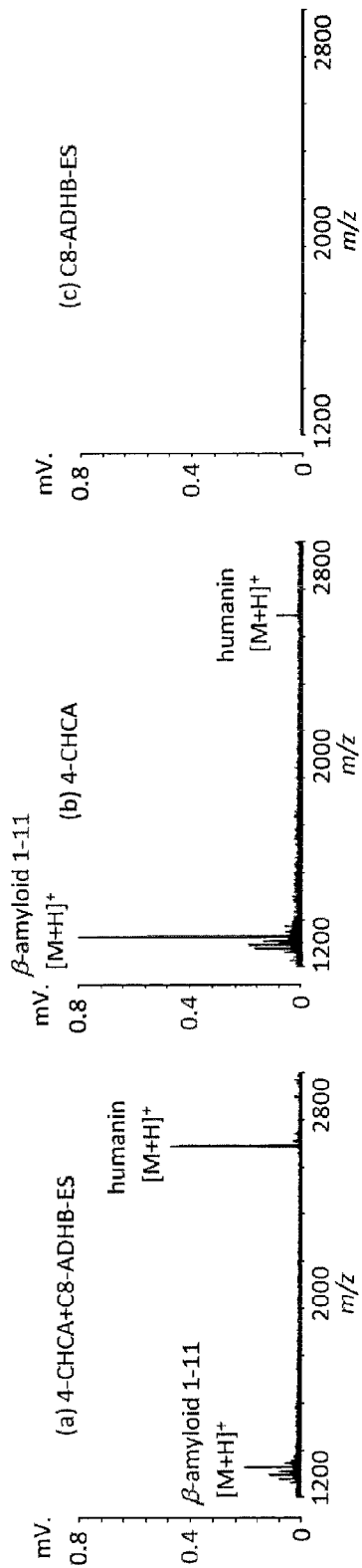
FIG. 4(a) shows the result of mass spectrometry using 4-CHCA+C8-ADHB-ES in Example 6.
FIG. 4(b) shows the result of mass spectrometry using 4-CHCA alone in Example 6.
FIG. 4(c) shows the result of mass spectrometry using C8-ADHB-ES alone in Example 6.

A mass spectrum in this case is shown in FIG. 4(a).

Comparative Example (1) A 10 mg/mL 4-CHCA solution (in an aqueous 50% ACN/0.05% TFA solution) and a 5 mg/mL C8-ADHB-ES solution (in an aqueous 50% ACN/0.05% TFA solution) were prepared.

(2) A 40 fmol/μL solution (in an aqueous 50% ACN/0.05% TFA solution) of a hydrophobic peptide humanin and a 40 fmol/μL, solution (in an aqueous 50% ACN/0.05% TFA solution) of a hydrophilic peptide β-amyloid 1-11 were prepared and mixed in a ratio of 1:1 (v/v) to prepare a mixed solution.

(3) The sample solution (0.5 μL) prepared in (2) and each of the matrix solutions (0.5 μL) prepared in (1) were dropped onto a MALDI plate and mixed (on-target mix).

(4) Analysis was performed using AXIMA Performance (Shimadzu Corporation) by linear TOF in positive mode.

Mass spectra in this case are shown in FIG. 4(b) (in the case of using 4-CHCA alone) and FIG. 4(c) (in the case of using C8-ADHB-ES alone).

As can be seen from FIGS. 4(a), 4(b), and 4(c), the sensitivity of the hydrophobic peptide humanin was improved when 4-CHCA+C8-ADHB-ES was used as compared to when 4-CHCA was used alone, and the hydrophobic peptide humanin was detected with higher sensitivity than the hydrophilic peptide β-amyloid 1-11 when 4-CHCA+C8-ADHB-ES was used. On the other hand, when C8-ADHB-ES was used alone, neither ions of β-amyloid 1-11 nor ions of humanin were detected. This revealed that the sensitivity of the hydrophobic peptide was improved by the use of 4-CHCA+C8-ADHB-ES.

Example 7

In this example, 4-CHCA was used as a matrix and C8-ADHB-ES was used as an additive. For the purpose of comparison, analysis was also performed using 4-CHCA alone as a matrix.

(1) A 10 mg/mL solution (in an aqueous 50% ACN/0.05% TFA solution) of a matrix 4-CHCA and a 5 mg/mL C8-ADHB-ES solution (in an aqueous 50% ACN/0.05% TFA solution) were mixed in a ratio of 10:1 (v/v) to prepare a matrix solution (4-CHCA+C8-ADHB-ES).

(2) A 200 fmol/μL solution (in an aqueous 50% ACN/0.05% TFA solution) of a tryptic digest of Phosphorylase b was prepared.

(3) The sample solution (0.5 μL) prepared in (2) and the matrix solution (0.5 μL) prepared in (1) were dropped onto a MALDI plate and mixed (on-target mix).

(4) Analysis was performed using AXIMA Performance (Shimadzu Corporation) by linear TOF in positive mode.

Figure 5:
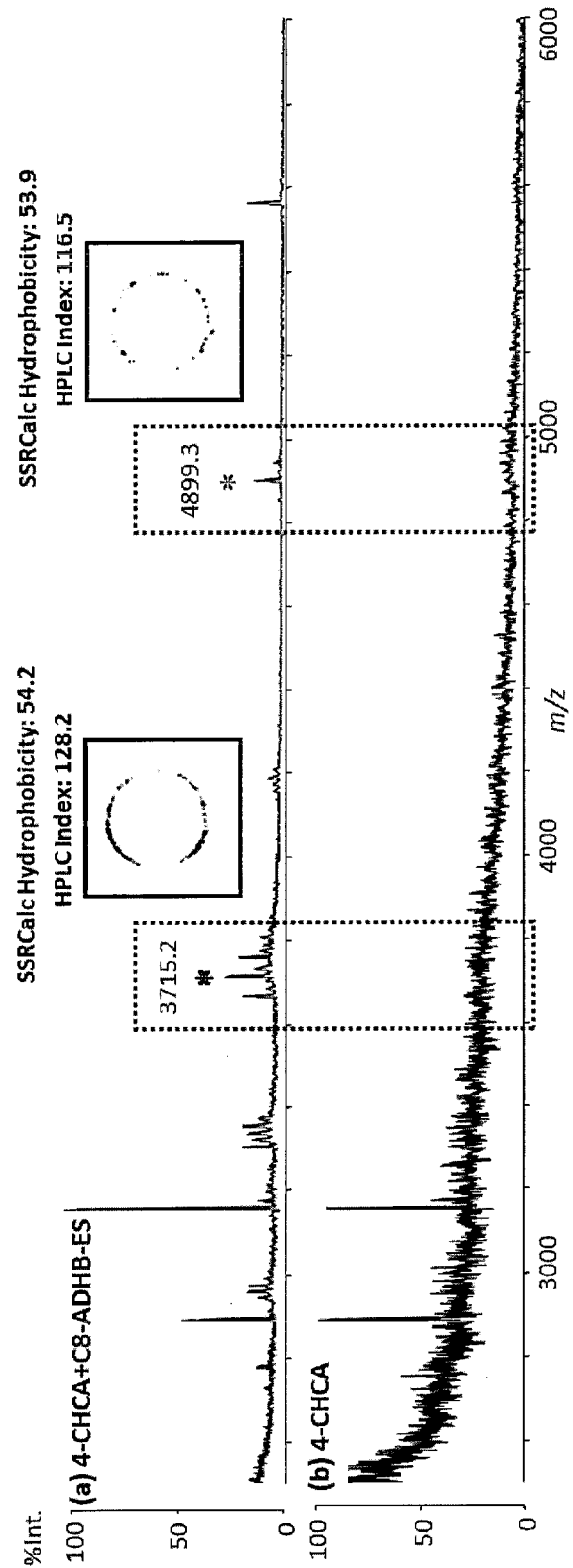
FIG. 5(a) shows the result of mass spectrometry using 4-CHCA+C8-ADHB-ES in Example 7 together with the results of MS imaging analysis (MS images) of peptide ions (m/z 3715.2 and m/z 4899.3)
FIG. 5(b) shows the result of mass spectrometry using 4-CHCA alone in Example 7.

A mass spectrum in this case is shown in FIG. 5(a) together with the results of MS imaging analysis (mass images) of peptide ions (m/z 3715.2 and m/z 4899.3).

Comparative Example (1) A 10 mg/mL 4-CHCA solution (in an aqueous 50% ACN/0.05% TFA solution) was prepared.

(2) A 200 fmol/μL solution (in an aqueous 50% ACN/0.05% TFA solution) of a tryptic digest of Phosphorylase b was prepared.

(3) The sample solution (0.5 μL) prepared in (2) and the matrix solution (0.5 μL) prepared in (1) were dropped onto a MALDI plate and mixed (on-target mix).

(4) Analysis was performed using AXIMA Performance (Shimadzu Corporation) by linear TOF in positive mode.

A mass spectrum in this case is shown in FIG. 5(b).

As shown in FIGS. 5(a) and 5(b), when 4-CHCA+C8-ADHB-ES was used, digest-derived peptide ions (m/z 3715.2 and m/z 4899.3) not detected when 4-CHCA was used alone were detected. These peptides were a hydrophobic peptide having an SSRCalc Hydrophobicity of 54.2 (HPLC index: 128.2) and a hydrophobic peptide having an SSRCalc Hydrophobicity of 53.9 (HPLC index: 116.5). The results of MS imaging shown in FIG. 5(a) revealed that the peptides were detected mainly in the outer peripheral region of a matrix/sample mixed crystal. This revealed that C8-ADHB-ES was effective also for the digest in enriching the hydrophobic peptides in the outer peripheral region of the matrix/sample mixed crystal and thereby improving sensitivity.

What is claimed is:

1. A MALDI mass spectrometry method for analysis of a sample to be analyzed comprising, hydrophobic substances, said method comprising the steps of:
obtaining a mixture liquid comprising, in a solvent, a sample to be analyzed, a matrix, and a matrix additive selected from the group consisting of a 2,5-dihydroxybenzoate and a 3,5-dihydroxybenzoate that are represented by the following formula (I):

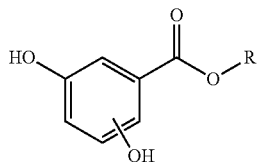

where R represents an alkyl group having 4 to 14 carbon atoms;
placing at least one liquid droplet of the mixture liquid on a target plate;
forming a mixed crystal for mass spectrometry by removing the solvent, wherein the hydrophobic substances of the sample to be analyzed are concentrated in an outer peripheral region of the mixed crystal, the outer peripheral region having an annular ring shape defined by concentric inner and outer edges, the outer edge of the outer peripheral region corresponding to an outer edge of the substantially circular shape and
irradiating at least the outer peripheral region of the mixed crystal with laser to detect the sample to be analyzed.

2. The MALDI mass spectrometry method according to claim 1,
wherein the mixed crystal for mass spectrometry has a substantially circular shape on a surface in contact with the target plate for mass spectrometry,
wherein an average outer diameter of the outer peripheral region is defined as an average length of all line segments that pass between two points on the outer edge of the outer peripheral region and through a center of the substantially circular shape, and an average inner diameter of the outer peripheral region is defined as an average length of all line segments that pass between two points on the inner edge of the outer peripheral region and through a center of the substantially circular shape, and the average inner diameter is 80% or more of the average outer diameter.

3. The MALDI mass spectrometry method according to claim 1, wherein the sample to be analyzed is a hydrophobic peptide.

4. The MALDI mass spectrometry method according to claim 1, wherein as the matrix, a compound is used which is selected from the group consisting of α-cyano-3-hydroxycinnamic acid (3-CHCA), α-cyano-4-hydroxycinnamic acid (4-CHCA), 3-hydroxy-4-nitrobenzoic acid (3H4NBA), 2,5-dihydroxybenzoic acid, sinapic acid, and 1,5-diaminonaphthalene.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: human

<400> SEQUENCE: 1

Gly Pro His Arg Ser Thr Pro Glu Ser Arg Ala Ala Val
1               5                   10